United States Patent [19]

Hurtel et al.

[11] Patent Number: 4,859,796
[45] Date of Patent: Aug. 22, 1989

[54] REACTING A (METH)ACRYLIC ANHYDRIDE WITH A DIAMINE TO FORM A N-DIALKYLAMINOALKYL(METH)ACRYLAMIDE

[75] Inventors: Patrice Hurtel; Denis Laurent, both of Saint Avold, France

[73] Assignee: Norsolor, Paris, France

[21] Appl. No.: 935,352

[22] Filed: Nov. 26, 1986

[30] Foreign Application Priority Data

Nov. 27, 1985 [FR] France .................. 85 17506

[51] Int. Cl.$^4$ ................ C07C 103/64; C07C 102/00; C07C 103/60; C08F 20/60
[52] U.S. Cl. .................................... 564/204; 564/206; 564/4
[58] Field of Search ......................................... 564/204

[56] References Cited

U.S. PATENT DOCUMENTS

| | | | |
|---|---|---|---|
| 2,567,836 | 9/1951 | Anthes | 564/204 X |
| 2,595,907 | 5/1952 | Thomas et al. | 564/204 X |
| 4,031,138 | 6/1977 | Nieh et al. | 564/205 X |

FOREIGN PATENT DOCUMENTS

| | | | |
|---|---|---|---|
| 0117530 | 9/1984 | European Pat. Off. | 564/204 |
| 2246538 | 5/1975 | France | 564/204 |
| 56-118049 | 9/1981 | Japan | 564/204 |
| 61-68456 | 4/1986 | Japan | 564/204 |
| 2037738 | 7/1980 | United Kingdom | 564/204 |

OTHER PUBLICATIONS

Besecke I, Chemical Abstracts, vol. 104, #169017n (1986).
Besecke II, Chemical Abstracts, vol. 105, #115527f (1986).
Blaschke et al., Ber. Deut. Chem. Gesell., vol. 108, pp. 2792 to 2798 (1975).
Narita et al., Chemical Abstracts, vol. 88, #90087c (1978).

*Primary Examiner*—Floyd D. Nigel
*Attorney, Agent, or Firm*—Millen, White & Zelano

[57] ABSTRACT

The present invention relates to a process for the preparation of an N-dialkylaminoalkyl(meth)acrylamide of formula:

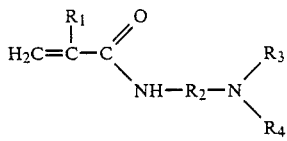

in which:
$R_1$ is a methyl radical or a hydrogen atom,
$R_2$ is a straight-chain or branched alkyl group containing at most 10 carbon atoms
$R_3$ and $R_4$, which are identical or different, may be:
  either two aliphatic alkyl groups containing from 1 to 4 carbon atoms,
  or $R_3$ is an aliphatic alkyl group containing from 1 to 4 carbon atoms and $R_4$ is an alicyclic group containing from 5 to 6 carbon atoms,
  or $R_3$ and $R_4$ are two alicyclic groups containing from 5 to 6 carbon atoms,
  or $R_3$ and $R_4$ form, together with the nitrogen atom to which they are chemically linked, a heterocycloaliphatic group.

This process is characterized in that a (meth)acrylic anhydride of formula:

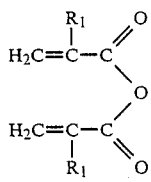

is reacted with a diamine of formula:

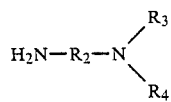

in the presence of a polymerization inhibitor.

8 Claims, No Drawings

# REACTING A (METH)ACRYLIC ANHYDRIDE WITH A DIAMINE TO FORM A N-DIALKYLAMINOALKYL(METH)ACRYLAMIDE The present invention relates to a new process for the synthesis of an N-dialkylaminoalkyl(meth)acrylamide, that is to say of N-dialkylaminoalkylmethacrylamides and of N-dialkylaminoalkylacrylamides.

An N-dialkylaminoalkyl(meth)acrylamide is defined as a compound of the general formula:

$$H_2C=C(R_1)-C(=O)-NH-R_2-N(R_3)(R_4)$$

in which:
$R_1$ is a methyl radical or a a hydrogen atom,
$R_2$ is a straight-chain or branched alkyl group containing at most 10 carbon atoms,
$R_3$ and $R_4$, which are identical or different from each other, may be:
  either two aliphatic alkyl groups containing from 1 to 4 carbon atoms,
  or, $R_3$ is an aliphatic alkyl group containing from 1 to 4 carbon atoms and $R_4$ is an alicyclic group containing from 5 to 6 carbon atoms, or $R_3$ and $R_4$ are two alicyclic groups containing from 5 to 6 carbon atoms,
  or $R_3$ and $R_4$ form, together with the nitrogen atom to which they are chemically linked, a heterocycloaliphatic group which may be, in particular, piperidine or pyrrolidine.

BACKGROUND OF THE INVENTION

Several synthetic routes to these compounds are well known at present. In particular, there are known reactions which involve a methacrylic acid, or its esters, and an amine. This type of reaction has the severe disadvantage of competing with a secondary reaction: this is the Michael reaction, that is to say the addition of the amine to the (meth)acrylic double bond. For this reason, the various processes for the synthesis of an N-dialkylaminoalkyl(meth)acrylamide are complex processes consisting of several reaction steps.

Thus, the process described in U.S. Pat. No. 3,878,247 and Canadian Pat. No. 1,020,163 involves reacting a diamine of formula $(R_2)(R_3)N-(CH_2)_n-NH_2$ (where $R_2$ and $R_3$ are, in particular, alkyl groups) with an acid or an ester of the formula $H_2C=CR_1-COOZ$ (where $R_1$ is a methyl radical or a hyrogen atom, and Z is a hydrogen atom or an alkyl group). This reaction gives an intermediate product, resulting from the amidification of the acid group or of the ester group of the (meth)acrylic derivative, and from the Michael addition of the diamine to the methacrylic double bond. This is the $\beta$-aminopropionamide of formula:

$$(R_2)(R_3)N-(CH_2)_n-NH-CH_2-CH(R_1)-CO-NH-(CH_2)_n-N(R_2)(R_3)$$

The thermal decomposition of this intermediate product at 210°–250° C., in the presence of a catalyst (U.S. 3,878,247), or without a catalyst but at 180°–300° C. (CA. 1,020,163), yields the N-dialkylaminoalkyl(meth)acrylamide.

There are also known processes for the synthesis of an N-dialkylaminoalkyl(meth)acrylamide in which the Michael reaction is avoided.

According to a first such process, which is described, in particular, in German Patent No. 2,856,383 and in European Patent No. 13,416, an amide of a $\beta$-hydroxycarboxylic acid is reacted with an amine and the intermediate product is then dehydrated at a temperature of between 200° and 400° C., ultimately to yield the desied (meth)acrylamide.

Another process involves using a catalyst which inhibits the Michael reaction of the amine with the double bond of the (meth)acrylic ester. The recommended catalysts in a reaction of this type are, in particular, organostannous compounds in U.S. Pat. No. 4,321,411, dialkyltin oxides in German Pat. No. 2,816,516, or alternatively alkyl titanates in German Pat. No. 3,048,020. The use of this process requires precautions so as not to poison the catalyst.

SUMMARY OF THE INVENTION

The present invention, whose aim is to solve the problems of the known processes, offers a new process which is simple to implement and which makes it possible to produce substituted (meth)acrylamides without any traces of secondary products, in high yields.

More precisely, the present invention relates to a new process for the synthesis of an N-dialkylaminoalkyl(meth)acrylamide of formula:

$$H_2C=C(R_1)-C(=O)-NH-R_2-N(R_3)(R_4)$$

in which:
$R_1$ is a methyl radical or a hydrogen atom,
$R_2$ is a straight-chain or branched alkyl group containing at most 10 carbon atoms, and
$R_3$ and $R_4$, which are identical or different, may be:
  either two aliphatic alkyl groups containing from 1 to 4 carbon atoms,
  or $R_3$ is an aliphatic alkyl group containing from 1 to 4 carbon atoms and $R_4$ is an alicyclic group containing from 5 to 6 carbon atoms,
  or $R_3$ and $R_4$ are two alicyclic groups containing from 5 to 6 carbon atoms,
  or $R_3$ and $R_4$ form, together with the nitrogen atom to which they are chemically linked, a heterocycloaliphatic group which may be piperidine or pyrrolidine,
which process is characterized in that a (meth)acrylic anhydride of formula:

$$(H_2C=C(R_1)-C(=O))_2O$$

is reacted with a diamine of formula

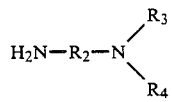

in the presence of at least one polymerization inhibitor at a temperature of between 70° and 100° C. and in the presence of oxygen, and the N-dialkylaminoalkyl(meth)acrylamide formed is then separated.

DETAILED DISCUSSION

Unexpectedly, the process according to the invention makes it possible to obtain high yields of N-dialkylaminoalkyl(meth)acrylamide, higher than 80%, with short reaction times which are generally between 15 and 30 minutes.

In fact, the presence of oxygen in the reaction environment makes it possible to inhibit the polymerization of the unsaturated compounds which are present, namely N-dialkylaminoalkyl(meth)alcrylamide and (meth)acrylic anhydride, even though the reaction temperature may be high. In addition, the final product obtained has good storage stability. The oxygen used in the process according to the invention may be introduced, for example, by performing the reaction in the presence of air or alternatively by providing a steam of oxygen in the reaction environment.

Among the polymerization inhibitors which may be used in the process according to the invention, there may be mentioned hydroquinone, hydroquinone methyl ether, phenothiazine, 2,6-tert-butyl-p-cresol, or methylene blue or copper salts such as copper sulphate, copper acetate or cupric chloride, in a weight ratio greater than or equal to 0.25% relative to the (meth)acrylic anhydride.

In accordance with an embodiment, the separation of the N-dialkylaminoalkyl(meth)acrylamide is produced by neutralization of the (meth)acrylic acid formed, using a strong base, for example sodium hydroxide, followed by extraction of the N-dialkylaminoalkyl(meth)acrylamide with an organic solvent. According to the invention, solvents of the benzene type are preferably used, for example benzene or toluene.

According to another preferred embodiment of the invention, the N-dialkylaminoalkyl(meth)acrylamide is separated by distillation, this operation being performed in the presence of oxygen. In this case, it has been found that the separation of the N-dialkylaminoalkyl(meth)acrylamide is perfect if, before and/or after the reaction between the (meth)acrylic anhydride and the diamine, there is added to the reaction mixture a solvent which is inert towards the reaction mixture, which forms a homogeneous mixture with the latter and which has a boiling temperature lying between that of (meth)acrylic acid and that of the N-dialkylaminoalkyl(meth)acrylamide. The reaction mixture obtained after the reaction, which comprises essentially (meth)acrylic acid and the N-dialkylaminoalkyl(meth)acrylamide is, in fact, viscous. The reaction products cannot be successfully and properly separated by distillation and it is found that impurities originating from the polymerization of these products are present. Now, it has been found that the presence of an inert solvent whose boiling temperature is intermediate between that of (meth)acrylic acid and that of the N-dialkylaminoalkyl(meth)acrylamide enables the products of the reaction to be perfectly separated by distillation and pure N-dialkylaminoalkyl(meth)acrylamide to be ultimately obtained. This solvent is added to the reaction mixture in a proportion of 10 to 50% by weight based on the total charge of the reactants, and preferably in a proportion of 20 to 30% by weight based on the total charge of the reactants.

Among the solvents which can be used in the process according to the invention there may be mentioned 1,2,4-trichlorobenzene and its isomers, 1,2-dichlorobenzene and its isomers, or esters, for example phenyl acetate, octyl acetate, terpenyl acetate or tetrahydrofurfuryl acetate, as long as the boiling temperature of these solvents has a boiling point which is intermediate between those of the acid and of the amide wich are formed during the reaction.

The anhydrides to which the process according to the invention applies are, in particular, methacrylic anhydride and acrylic anhydride.

Among the diamines of formula

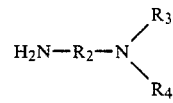

which can be used in the process according to the invention there may be mentioned, in particular: N,N-dimethylaminoethylenediamine, N,N-dimethylaminotrimethylene-1,3-diamine, N,N-dimethylaminotetramethylene-1,4-diamine, N,N,2,2-tetramethylpropane-1,3-diamine, piperidinyl-N-alkylamine or pyrrolidinyl-N-alkylamine, aminoethylimidazolidone, and the like.

The molar ratio of the (meth)acrylic anhydride to the diamine is preferably chosen between 1 and 1.2.

The reaction according to the invention is also preferbly carried ot at atmospheric pressure.

The process according to the invention is advantageous in more than one way.

The process according to the invention consists of only a single reaction step, and this makes it easier to develop on an industrial scale.

Furthermore, as indicated earlier, the process according to the invention makes it possible to obtain high yields of N-dialkylaminoalkyl(meth)acrylamide, above 80% in most cases.

EXAMPLES

The examples which are given below, by way of indication and without implying any limitation, will enable the invention to be better understood. All the tests described in these examples are carried out at atmospheric pressure, and thus in the presence of air. The separation of the product obtained by distillation is performed at reduced pressure, provision being made for oxygen to be bubbled into the reaction mixture.

EXAMPLE 1

Preparation of dimethylaminopropylmethacrylamide

The following charge is introduced into a reactor fitted with a condensing device and a mechanical stirring system:
154 g of methacrylic anhydride,
B 0.75 g of methylene blue, and
0.75 g of copper acetate.

When the temperature of the reaction mixture reaches 75° C. at atmospheric pressure, the following are run into this mixture:
102 g of N,N-dimethylaminopropylamine, and 77 g of 1,2,4-trichlorobenzene.

After the reaction, which takes place virtually instantaneously when the reactants come into contact, 0.75 g of phenothiazine and 0.75 g of 2,6-tert-butyl-p-cresol are added, and the reaction mixture is distilled under vacuum. The methacrylic acid which has formed during the reaction is distilled as forerunnings. The methacrylic acid comes over at 88° C. at a pressure for 40 mm Hg. 86 g of methacrylic acid are collected. 1,2,-4-trichlorobenzene is then distilled at 65° C. at a pressure of 4 mm Hg. Dimethylaminopropylmethacrylamide is then recovered at 124° C. at 4 mm Hg. 156.7 g of dimethylaminopropylmethacrylamide are collected.

The yield is 88%.

EXAMPLE 2

Preparation of dimethylaminoneopentylacrylamide

The following charge is introduced into the reactor in an apparatus which is identical to that described in Example 1:
189 g of acrylic anhydride.
195 g of N,N,2,2-tetramethylpropane-1,3-diamine,
115 g of 1,2,4-trichlorobenzene,
0.75 g of methylene blue, and
0.75 g of copper sulhate.

The reaction is conducted with stirring at a temperature of 75° C. and at atmospheric pressure. After the reaction, which takes place virtually instantaneously when the reactants come into contact, the following are added to the reaction mixture:
0.75 g of phenothiazine,
0.75 g of N,N'-phenyl-para-phenylenediamine, and
0.75 g of hydroquinone methyl ether.

The reaction products are then separated by distillation. The forerunnings consist of acrylic acid, which comes over at 81° C. at 100 mm Hg. 108 g of acrylic acid are collected. 1.2,4-trichlorobenzene, which comes over at 65° C. at 4 mm Hg is distilled next. Dimethylaminoneopentylacrylamide is then recovered at 131° C. at 8 mm Hg. 226 g of dimethylaminoneopentylacrylamide are collected.

The yield is 82%.

EXAMPLE 3

Preparation of dimethylaminopropylacrylamide

The following charge is introduced into the reactor in an apparatus which is identical to that described in Example 1:
204 g of N,N-dimethylaminopropylamine,
137 g of 1,2,4-trichlorobenzene, and
3,000 ppm of methylene blue.

252 g of acrylic anhydride are then poured into the reactor, the temperature in the reactor being 80° C. After the reaction, which takes place virtually instantaneously when the reactants come into contact, 1,500 ppm of hydroquinone methyl ether and 1,500 ppm of phenothiazine are added, and the reaction mixture is distilled under a vacuum. The forerunnings consist of acrylic acid which has been formed during the reaction. Acrylic acid comes over at 81° C. at a pressure of 100 mm Hg. 144 g of acrylic acid are collected. 1,2,4-trichlorobenzene is distilled next at 78° C. at a pressure of 5 mm Hg. Dimethylaminopropylacrylamide is then recovered at 129° C. at 3 mm Hg. 270.8 g of dimethylaminopropylacrylamide are collected.

The yield is 90%.

EXAMPLE 4

Preparation of methacrylamidoethylimidazolidone

The following charge is introduced into a reactor fitted with a condensing device and a mechanical stirring system:
485.1 g of methacrylic anhydride,
500 g of 1,2,4-trichlorobenzene,
500 ppm of phenothiazine, and
1,000 ppm of hydroquinone methyl ether.

The reaction mixture formed in this manner is stirred intensively; 387 g of aminoethylimidazolidone are then added.

Throughout the reaction period, the reaction mixture is kept at atmospheric pressure and the temperature is maintained at 75° C.

The methacrylic acid formed during the reaction is distilled off in the presence of air. This comes over at 82° C. at a pressure of 30 mm Hg. The mixture of trichlorobenzene and methacrylamidoimidazolidone is then cooled. Crystals of methacrylamidoimidazolidone precipitate and are then filtered off, washed with acetone and then dried.

450 g of the required monomer are thus collected.
Melting point: 114° C.
Yield: 76%.

We claim:

1. A process for the synthesis of a N-dialkylaminoalkyl(meth)acrylamide of the formula:

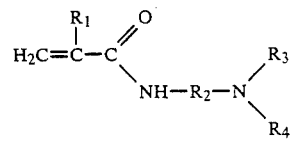

in which:
R₁ is methyl or hydrogen,
R₂ is alkyl group containing at most 10 carbon atoms,
R₃ and R₄, being identical or different, each represent an: aliphatic alkyl group containing from 1 to 4 carbon atoms, or an alicyclic group containing from 5 to 6 carbon atoms; or R₃ or R₄, together with the nitrogen atom to which they are chemically linked, represent piperidino or pyrrolidino,
which process comprises reacting a (meth)acrylic anhydride of the formula:

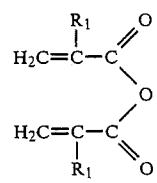

with a diamine of the formula:

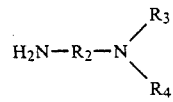

in the presence of at least one polymerization inhibitor at a temperature of between 70° and 100° C. and in the presence of oxygen, and separating resultant N-dialkylaminoalkyl(meth)acrylamide.

2. A process according to claim 1 wherein the N-dialkylaminoalkyl(meth)acrylamide obtained is separated by distillation and in that, before the reaction between (meth)acrylic anhydride and the diamine, after said reaction, or both before and after said reaction, there is added to the reaction mixture an organic solvent which is inert to the reaction mixture, which forms a homogeneous mixture with the latter, and which has a boiling temperature lying between that of (meth)acrylic acid and that of the N-dialkylaminoalkyl(meth)acrylamide.

3. Process according to claim 2, characterized in that the quantity of solvent which is introduced into the reaction mixture is between 10 and 50% by weight based on the total charge of the reactants.

4. Process according to claim 3, characterized in that the quantity introduced into the reaction mixture is between 20 and 30% by weight based on the total charge of the reactants.

5. A process according to claim 1, wherein the inert solvet is 1,2,4-trichlorobenzene.

6. A process according to claim 1, wherein the N-dialkylaminoalkyl(meth)acrylamide obtained is separated by extraction with an organic solvent after neutralization of the reaction mixture using a strong base.

7. A process according to claim 1, wherein the molar ratio of (meth)acrylic anhydride to the diamine is between 1 and 1.2.

8. A process according to claim 1, wherein the quantity of polymerization inhibitor is such that the weight ratio of this inhibitor to the (meth)acrylic anhydride is at least 0.25%.

* * * * *

UNITED STATES PATENT AND TRADEMARK OFFICE
CERTIFICATE OF CORRECTION

PATENT NO. : 4,859,796

DATED : August 22, 1989

INVENTOR(S) : HURTEL ET AL

It is certified that error appears in the above-identified patent and that said Letters Patent is hereby corrected as shown below:

Column 7, line 1 of claim 3:
    reads "Process according to claim 2, characterized in that"

should read -- A process according to claim 2, wherein --

Column 8, claim 4, line 1:
    reads "Process according to claim 3, characterized in that"

should read -- A process according to claim 3, wherein --

Signed and Sealed this

Twelfth Day of June, 1990

Attest:

HARRY F. MANBECK, JR.

*Attesting Officer*      *Commissioner of Patents and Trademarks*